United States Patent
Ma et al.

(10) Patent No.: US 7,563,228 B2
(45) Date of Patent: Jul. 21, 2009

(54) STEREOSCOPIC THREE OR FOUR DIMENSIONAL ULTRASOUND IMAGING

(75) Inventors: Qinglin Ma, Bellevue, WA (US); Robert N. Phelps, Fall City, WA (US); Gerald A. Raitzer, Seattle, WA (US); Jerry D. Hopple, Woodinville, WA (US); Steven R. Marquis, Fall City, WA (US); David A. Waataja, Seattle, WA (US); Carol M. Lowery, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 788 days.

(21) Appl. No.: 11/042,888

(22) Filed: Jan. 24, 2005

(65) Prior Publication Data

US 2006/0173338 A1    Aug. 3, 2006

(51) Int. Cl.
A61B 8/00 (2006.01)
G09G 5/00 (2006.01)
H04N 13/04 (2006.01)

(52) U.S. Cl. .......... 600/437; 359/466; 348/51; 600/443

(58) Field of Classification Search .......... 600/440, 600/437, 443; 375/240.25; 358/88; 359/466; 382/154

See application file for complete search history.

(56) References Cited

U.S. PATENT DOCUMENTS

| 4,486,076 | A |   | 12/1984 | Taenzer |
|---|---|---|---|---|
| 4,559,555 | A | * | 12/1985 | Schoolman ............ 348/53 |
| 4,647,966 | A |   | 3/1987 | Phillips et al. |
| 4,967,268 | A |   | 10/1990 | Lipton et al. |
| 5,054,045 | A |   | 10/1991 | Whiting et al. |
| 5,281,957 | A |   | 1/1994 | Schoolman |
| 5,457,728 | A |   | 10/1995 | Whiting et al. |
| 5,488,952 | A |   | 2/1996 | Schoolman |
| 5,822,391 | A |   | 10/1998 | Whiting et al. |
| 5,993,391 | A |   | 11/1999 | Kamiyama |
| 6,400,394 | B1 |   | 6/2002 | Kim et al. |
| 6,416,476 | B1 |   | 7/2002 | Ogasawara et al. |
| 2002/0113756 | A1 | * | 8/2002 | Tuceryan et al. .......... 345/8 |
| 2003/0139671 | A1 |   | 7/2003 | Walston et al. |
| 2003/0223499 | A1 | * | 12/2003 | Routhier et al. ...... 375/240.25 |
| 2005/0283075 | A1 |   | 12/2005 | Ma et al. |
| 2006/0164411 | A1 | * | 7/2006 | Lee .................... 345/419 |

OTHER PUBLICATIONS

Esaote Releases Picus-Just 3D dated Dec. 17, 2004, printed on Jan. 10, 2005.

(4) Esaote Web Pages; http://www.esaote.com/products/ultrasound/advanceTech/c3d.htm; http: www.esaote.com/products/ultrasound/TECHNOS/cAdvApplic3d.htm; http://www.esaote.com/products/ultrasound/picus/c3D.htm; and http://www.esaote.com/products/ultrasound/picus/cAdvantages.htm; all printed on Jan. 10, 2005.

(Continued)

*Primary Examiner*—Eric F Winakur
*Assistant Examiner*—Lawrence N Laryea (57) ABSTRACT

Medical diagnostic ultrasound stereo imaging is provided. A medical diagnostic ultrasound system operable to scan a body with ultrasound is also operable to generate a three dimensional stereoscopic view of the body. The video processing unit and/or display device create the stereoscopic display.

21 Claims, 3 Drawing Sheets

OTHER PUBLICATIONS

"FOE From Motion Parallax," by Edelman Shimon dated Dec. 26, 1995; http://kybele.phsch.cornell.edu/~edelman/Course/motion/node36.html; printed on Jan. 11, 2005.

"Subjective Assessments of Dynamic Visual Noise Interference in 3D TV Picture," Pastoor, S. and I.P. Beldie; Proceedings of the Society for Information Display; vol. 30, No. 3, 1989.

"Evaluation of Stereoscopic Display Benefits," by J. Merritt; SPIE 2002 Stereoscopic Display Application Issues lecture notes.

"A Rapid-Sequential-Positioning Task for Evaluating Motion Parallax and Steroscopic 3D Cues in Teleoperator Displays," by J. Merritt and R.E. Robert; Presented at IEEE 1991 Conference on Systems, Man and Cybernetics, Oct. 13-16 at the University of Virginia, Charlottesville.

"3D Video Standards Conversion," by A.J. Woods, T.M. Docherty and R. Koch; in Steroscopic Displays and Virtual Reality Systems III, Proceedings of the SPIE vol. 2653, 1996.

"Image Distortions in Steroscopic Video Systems," A.J. Woods, T.M. Docherty and R. Koch; in Steroscopic Displays and Applications IV, Proceedings of the SPIE vol. 1915.

"A Computer System for Visualizing Three-Dimensional Ultrasound Images as Steropairs," by Ylitalo et al.; IEEE Ultrasonics Symp., (Oct.-Nov. 1983), vol. 2, 722-725.

* cited by examiner

STEREOSCOPIC THREE OR FOUR DIMENSIONAL ULTRASOUND IMAGING

BACKGROUND

The present invention relates to three dimensional imaging. In particular, ultrasound images represent a volume.

A three dimensional representation is displayed on a CRT or flat panel monitor as a two dimensional image. Limited three dimensional effects or depth perception are achieved by various rendering methods, such as opacity, smooth filtering, shading, edge enhancing and other techniques.

Various kinds of stereoscopic images have emerged for computer game, flight simulation, movie and television. These products provide stereoscopic views of a three dimensional object at video display rates. The three dimensional effect is improved as compared to a two-dimensional image of a three-dimensional representation.

Three dimensional stereoscopic images have been used in general medical imaging and training. Stereoscopic ultrasound images have been created and displayed using offline products, such as a workstation separate from an ultrasound imaging system. Vivid ultrasound fetus stereoscopic images were created using a Siemens SXD3 3D color flat panel stereoscopic display monitor.

BRIEF SUMMARY

By way of introduction, the preferred embodiments described below include methods and systems for medical diagnostic ultrasound stereo imaging in three dimensions. A medical diagnostic ultrasound system operable to scan a body with acoustic energy is also operable to generate a three dimensional stereoscopic view of the body. The video processing unit and/or display device create the stereoscopic display.

In a first aspect, a system is provided for medical diagnostic ultrasound imaging. An ultrasound imaging system is operable to generate data representing a body with an ultrasound transducer. The ultrasound imaging system includes a three dimensional image processor operable to render first and second three-dimensional representations as a function of the data. The first and second three-dimensional representations correspond to first and second different viewing angles, respectively to simulate the left and right eye view. A stereoscopic display displays the first and second three-dimensional representations either simultaneously or sequentially at a high refresh rate.

In a second aspect, a method is provided for medical diagnostic ultrasound imaging. Ultrasound data representing a region is acquired with an ultrasound imaging system. First and second three-dimensional representations of the region are rendered with the ultrasound imaging system from first and second, different viewing directions, respectively. A stereoscopic display of the region is generated by the ultrasound imaging system with the first and second three-dimensional representations.

In a third aspect, a system is provided for medical diagnostic ultrasound imaging. A medical diagnostic ultrasound imaging system has a video processing unit operable to output first and second three-dimensional representations of a same region at first and second viewing angles, respectively. A display is operable to display the first and second three-dimensional representations either simultaneously or sequentially. A head mounted device is operable in conjunction with the display to provide a stereoscopic display of the region.

The present invention is defined by the following claims, and nothing in this section should be taken as a limitation on those claims. Further aspects and advantages of the invention are discussed below in conjunction with the preferred embodiments and may be later claimed.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A stereoscopic video display system is integrated in an ultrasound imaging machine. The video path of a conventional ultrasound system may be different from a personal computer or workstation. One difference is that, in addition to a graphic card, an ultrasound system has an additional video processing unit. The additional video processing unit adds a graphic overlay with patient registration information, hospital information, imaging parameters, etc. to the image and manages the video output/input to other image display devices, such as transferring images to DICOM workstation, CD burner, optical drive, DVD burner, VCR and printers. The graphic card might be similar to that used by a personal computer or workstation, but the additional video processing unit is typically a custom designed device.

The strengths of an ultrasound imaging system compared to some other medical imaging modalities are real-time capability, mobility and lower cost. Enabling the stereoscopic viewing of ultrasound three dimensional (3D) images on an ultrasound system may improve the image quality, 3D effect (e.g., luster, scintillation, and surface sheen more visible), depth perception, signal-to-noise ratio, anatomy localization, work flow, through put and/or the ability to view anatomy in real-time stereoscopically (e.g., four dimensional (4D) or 3D as a function of time). Stereoscopic ultrasound 3D/4D images are generated with the ultrasound system instead of an offline personal computer or workstation.

Stereoscopic ultrasound images may be generated of the fetal face, fetal limbs, whole fetal body, gall bladder with stones, bladder, kidney vasculature, any vasculature images, neo-natal brain, transcranial imaging and heart. The additional depth information may allow faster and/or easier analysis of complex structures. A range of applications may be improved by providing three-dimensional images with an enhanced level of visual ambience. Such applications include surgical planning, a teaching and training tool, a virtual biopsy tool, providing foundation for virtual reality display of ultrasound images, and/or use in conjunction with "fly-through" display technology and virtual perspective camera view imaging.

Figure 1:
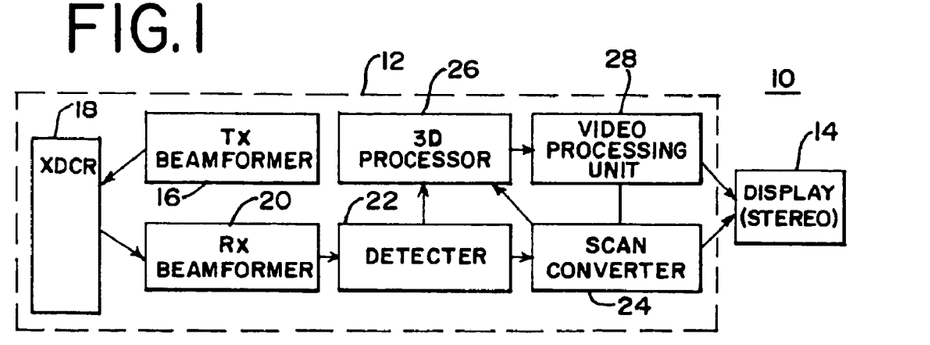
FIG. 1 is a block diagram of a first embodiment of a medical diagnostic ultrasound system for stereoscopic imaging.

FIG. 1 shows a system 10 for medical diagnostic ultrasound imaging. The system 10 includes an ultrasound imaging system 12 and a stereoscopic display 14. The ultrasound imaging system 12 is a medical diagnostic ultrasound imaging system operable to generate one or more images on the stereoscopic display 14. The ultrasound imaging system 12 includes a transmit beamformer 16, a transducer 18, a receive beamformer 20, a detector 22, a scan converter 24, a three-dimensional processor 26, and a video processing unit 28. Additionally, different or fewer components may be provided. For example, the three-dimensional processor 26 or the scan converter 24 are not provided. As another example, any of the three-dimensional processor 26, the scan converter 24, and the video processing unit 28 may be combined. The video processing unit 28 is operable to output multiple three-dimensional representations of a same region at different viewing angles. The different representations represent the region at a substantially same time from different viewing prospectives, such as associated with a left eye and a right eye, for stereoscopic display. Any ultrasound imaging system 12 may be used, such as cart based systems manufactured by Siemens, Philips, General Electric or Toshiba. Portable, hand-held or other now known or later developed medical diagnostic ultrasound imaging systems may be provided. The ultrasound imaging system 12 has the capability to acquire ultrasound data or scan a body, such as a patient, and generate corresponding images. For example, a sequence of images is provided in real-time using an ultrasound imaging system 12 while a sonographer positions a transducer on or within a patient.

Figure 2:
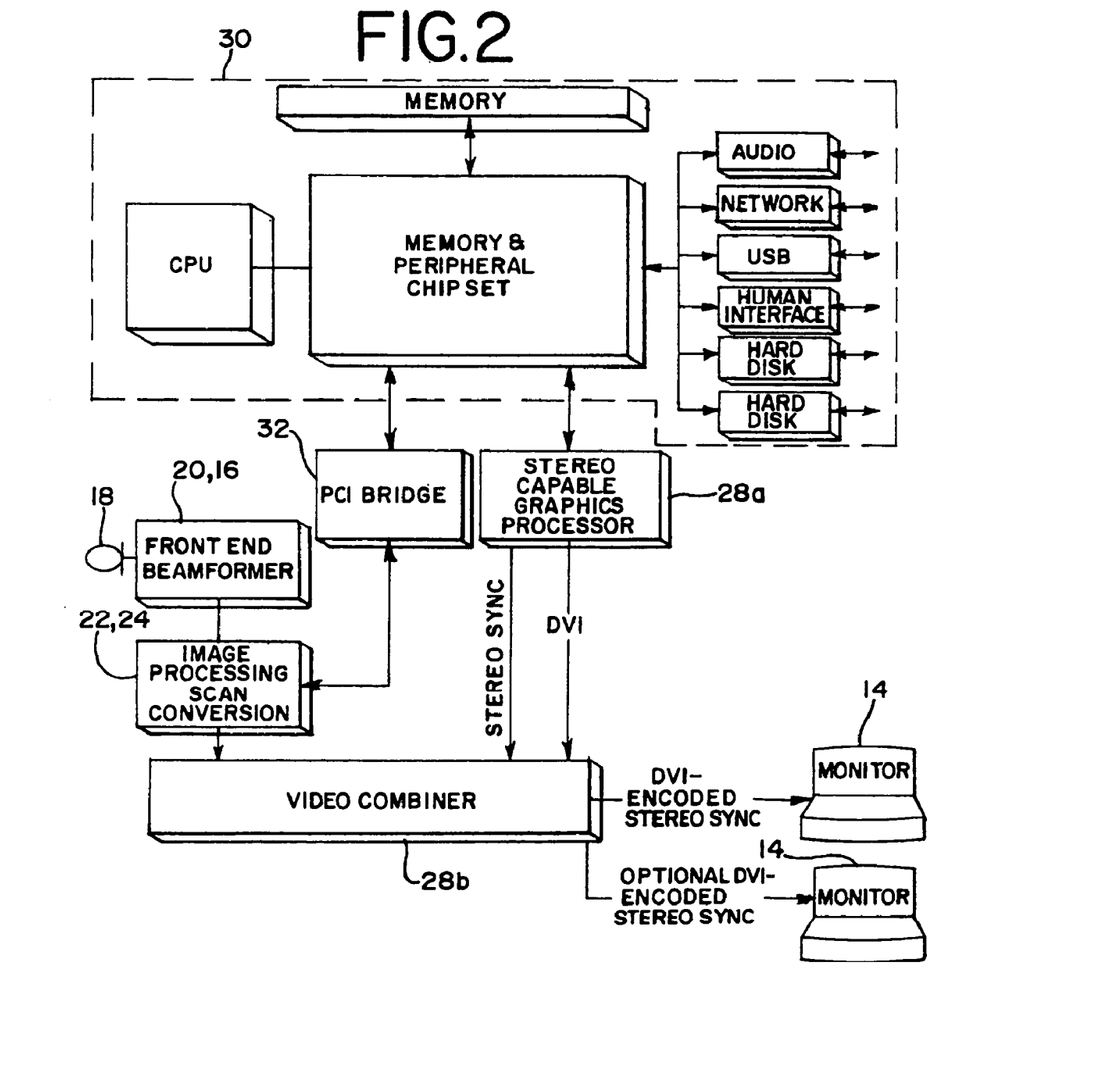
FIG. 2 is a block diagram of a second embodiment of a medical diagnostic ultrasound system for stereoscopic imaging.

FIG. 2 shows an alternative embodiment of the system 10 of FIG. 1. The video processing unit 28 is separated into two components, a stereo capable graphics processor 28A and a video combiner 28B. A personal computer type architecture 30 is provided for a control processor or central processing unit. The architecture 30 may be of any form, such as AGP architecture from Intel. The architecture 30 includes the central processing unit, a memory and peripheral chip set or bridge, a memory, a port or bus connection for any one or more of audio, network, USB, user input device (i.e., human interface), hard disk drive or other components. Another port or bridge is provided for connection to the stereo capable graphics processor 28A and/or a PCI bridge 32. The PCI bridge 32 connects the architecture 30 to the front end of the ultrasound imaging system 12. The front end beamformer 20, 16 performs transmit and receive beamforming operations. Some signal processing, such as base band filtering or synthetic line generation may also be performed by the front end beamformer 20, 16. Image processing and scan conversion is provided by a back end operating as the detector 22 and the scan converter 24. The detector 22 converts radio frequency or in-phase and quadrature signals to amplitude video signals for B-mode imaging or velocity, frequency, variance or energy for flow signals. Other image processing or filtering may be provided. The scan converter 24 converts the acquired data from an acquisition format to a two-dimensional Cartesian coordinate system for display on two-dimensional display devices. In alternative embodiments, the scan converter 24 is bypassed or operates as the three-dimensional processor 26.

The video combiner 28B may be hardwired or connected through a bus to the graphics processor 28. The video combiner 28B composites the image generated by the back end systems 22, 24 with a graphic overlay produced by the graphics processor 28A. The graphic overlay contains patient registration, hospital, sonographer, date, time, imaging parameter settings, or other information associated with a given image or sets of images. The graphics overlay may be textual, graphical or both textual and graphical. The combined information is then sent to an input/output board or otherwise provided for display on the stereoscopic display 14.

The transmit beamformer 16 generates transmit waveforms for operating in any of various modes, such as B-mode or flow mode. In response to the transmit waveforms, the transducer 18 generates acoustic energy. Echoes from the acoustically transmitted beam are received by the transducer 18. The resulting electrical signals are provided to the receive beamformer 20 for generating receive beams. Any of various scan formats, focused waveforms, plane waveforms, or other now known or later developed ultrasound scanning techniques may be used. The detector 22 detects an intensity, power, amplitude, frequency, velocity, energy, contrast agents, harmonic information, or other now known or later developed characteristic of the receive signals. The scan converter 24 converts the received information into a coordinate system for use by the display 14. In one embodiment, three-dimensional representations are rendered from scan converted information. In alternative embodiments, three-dimensional representations are rendered from data without scan conversion by the scan converter 24.

The three-dimensional processor 26 is a general processor, digital signal processor, application specific integrated circuit, field programmable gate array, digital circuit, graphics processing unit, graphics card, combinations thereof or other now known or later developed device for rendering three-dimensional representations. In the embodiment shown in FIG. 2, the three-dimensional processor 26 is implemented as the central processing unit of the architecture 30 or the back-end. For example, the CPU in conjunction with the graphics card 28A using open GL drivers or other drivers generates different views of a volume to simulate left and right eye viewing angles. The different views are generated by interpolating data from an acquisition grid to a three-dimensional reconstruction grid. Alternatively, the data remains in the acquisition format. Maximum, minimum, average, or other projection renderings may be used. For example, a plurality of lines parallel with the viewing angle is extended through a reconstructed three-dimensional grid. Data adjacent to or on each of the lines is used to determine a value for each pixel or line extending through the grid. The maximum, minimum, a closest value over a threshold, an average or other value along each line is selected. In alternative embodiments, surface renderings or other now known or later developed three-dimensional imaging technique are provided. By accounting for left and right eye positions, two different viewing angles may be defined for a same volume or three-dimensional reconstruction. Different three-dimensional representations are rendered as a function of the same data and correspond to the different viewing angles.

The three-dimensional processor 26 outputs three-dimensional representations associated with the two different viewing angles substantially simultaneously in parallel or sequence. As the user position alters with respect to the scan volume, one or both viewing angles change. With or without movement of the user's perspective, a continuing sequence of three-dimensional representations may be rendered for real time or 4D imaging. For sequential output, the representations associated with each of the viewing angles is output in pairs or other groupings to provide the views for each of the viewing angles at substantially the same time. The output rate for each viewing angle or for both viewing angles is synchronized with the video processing unit 28, the image frame display rate or combinations thereof.

Figure 3:
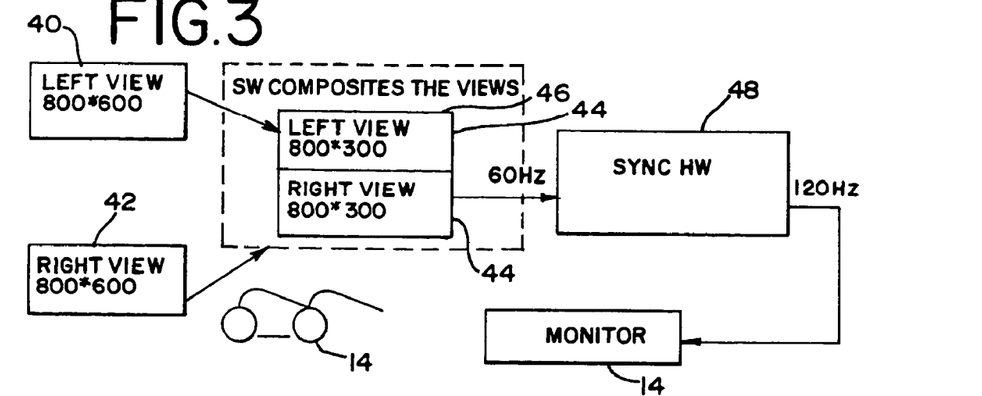
FIG. 3 is a graphical representation of one embodiment of stereoscopic viewing with an ultrasound system.

FIG. 3 shows one embodiment for stereoscopic viewing. The two different three-dimensional representations 40 and 42 are positioned within subfields 44 of a data frame 46. In the example shown, each of the representations 40, 42 is 800×600 pixels, but greater or lesser resolutions may be provided. The two different views are composited into top and bottom sub-frames 44. In alternative embodiments, the two different views are composited into left and right or other sub-frames. Through filtering, decimation, or other combinations, each of the views 40, 42 is reduced in resolution along one or more dimensions. Alternatively, the frame of data 46 has an increased resolution, such as associated with a lesser or no reduction in resolution. Each new frame of data 46 is reconstructed from both left and right views or representations 40, 42. In one embodiment, the three-dimensional processor 26 composites the two different representations 40, 42. In alternative embodiments, the video processing unit 28 composites the representations 40, 42. Each of the representations or the composite representation 46 may be compressed data, such as MPEG or AVI compressed data and DICOM compatible. Different images size, imaging rates or bit rates may be provided.

Since each output data frame 46 is associated with two different views 40, 42, the synchronization pulse rate is increased. For example, the vertical, horizontal or both vertical and horizontal synchronization pulses are output to synchronization circuitry 48. The synchronization circuit 48 is a transistors, processor, oscillator, phase locked loop, comparator, digital circuitry, analog circuitry or combinations thereof for increasing a synchronization rate associated with the data frame 46. For example where the sub-fields 44 are top and bottom sub-fields, the synchronization circuitry 48 detects the vertical synchronization pulse from the data frame 46. The vertical synchronization pulse rate is doubled. A pulse is generated in between each detected vertical synchronization pulse or two pulses are generated for each vertical synchronization pulse. For example, the data frame 46 is provided at 60 Hertz. The vertical synchronization pulse is then doubled to 120 Hertz. Where side-by-side sub-fields 44 are provided, their horizontal synchronization pulse is doubled for displaying the representations 40, 42 sequentially.

The data frame 46 and the altered synchronization information are passed to the video processing unit 28 as shown in FIGS. 1 and 2. The video processing unit 28 is a graphics processor, graphics card, video combiner, buffers, digital circuit, analog circuit, combinations thereof or other now known or later developed videos graphics devices for driving a display from input image data. In one embodiment, the synchronization circuit 48 is built into the video processing unit 28 or is separated. A single video channel is provided for inputting the data frame 46 and outputting to the monitor of the display 14. Since a composite data frame 46 is provided, the graphics processing unit 28 may operate at a normal 60 Hertz sync rate. Alternatively, an increased rate of operation may be provided.

The video processing unit 28 is operable to separate the different three-dimensional representations 40, 42 from the sub-fields 44 of the data frame 46. Extrapolation, interpolation or other processing may be used for increasing a resolution of each of the representations 40, 42, such as increasing resolution to 800×600 of the original representations 40, 42 from the reduced content data frame 46. In one embodiment, each line along one dimension is doubled and then low-pass filtered. After separating the representations 40, 42, the video processing unit 28 generates sequential display of the representations 40, 42 as a function of the increased synchronization rate. The left and right views are displayed in sequence at the original refresh rate of 60 Hertz. Since both views are displayed sequentially at 60 Hertz, 120 Hertz synchronization is provided.

Figure 4:
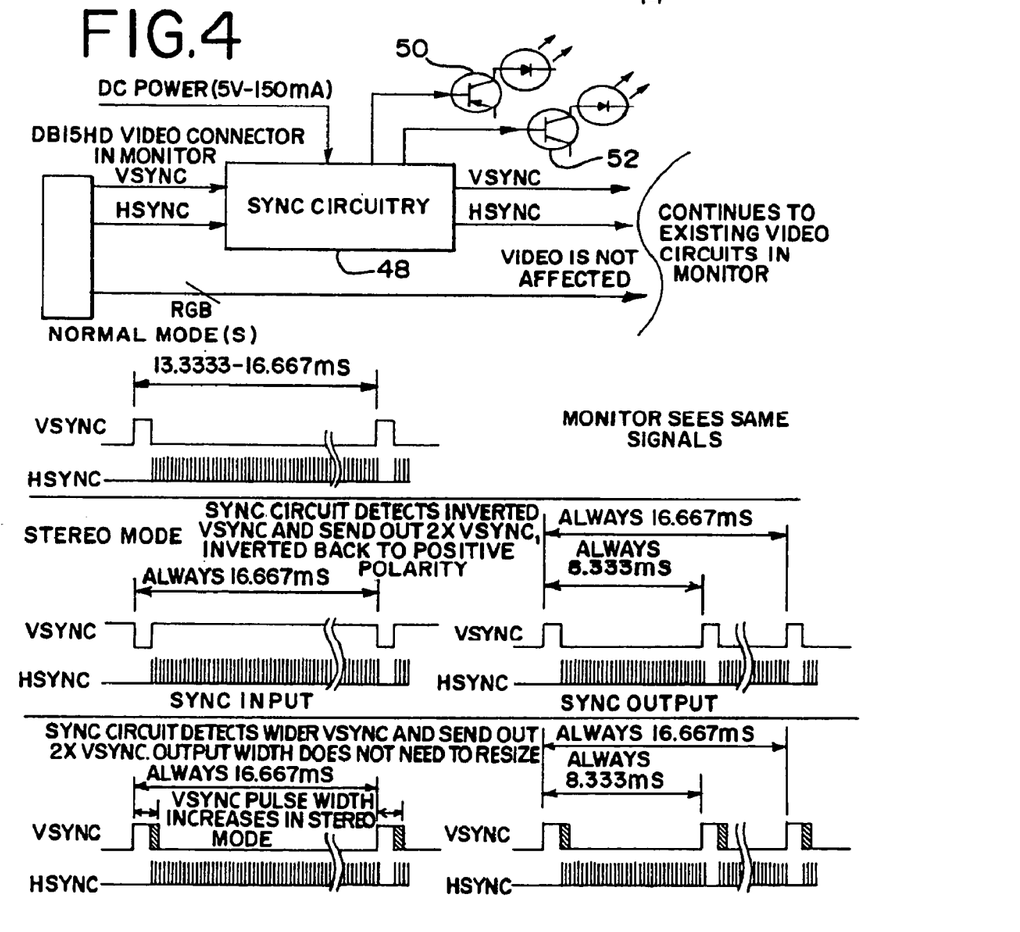
FIG. 4 is a graphical representation of one embodiment of a synchronization circuit.

As shown in FIG. 4, switches 50, 52 or other devices may be used for controlling the stereoscopic display 14 in synchronization with the generation of images. The synchronization circuitry 48 generates left and right synchronization signals. The synchronization signal is a direct signal, 50 percent duty cycle signal indicating left and right fields or a DVI signal included in a control channel. The switches operate in conjunction with infrared light emitting diodes to trigger shutter glasses in one embodiment. The switches 50, 52 are positioned adjacent to the light emitting diodes for rapid responsiveness. For monoscopic viewing, the switches 50, 52 are not operated, leaving the viewer able to view with both eyes simultaneously.

In one embodiment, the system 10 of FIGS. 1 or 2 provides the stereoscopic viewing without monoscopic viewing. Alternatively, the video processing unit 28 is operable in both stereoscopic and monoscopic modes. The mode of operation is selected by a user or defaults to a given mode, such as defaulting to stereoscopic viewing when a stereoscopic viewing device is attached to the ultrasound imaging system 12. For monoscopic operation, the circuitry used for stereoscopic operation is bypassed.

The video processing unit 28 is operable to select between stereoscopic and monoscopic modes as a function of a characteristic of the synchronization pulse output by the synchronization circuit 48 shown in FIGS. 3 and 4. In one embodiment, a hard switch or button independent of switches operable to control imaging software is provided for switching between monoscopic and stereoscopic modes. For example, a permanently encoded button or a software based selectable button is used to allow the user to switch regardless of other operations of the ultrasound imaging system 12. The switch activates switches or other devices for controlling operation of the video processing unit 28. Software may be used to electronically switch between modes in response to user input.

A dedicated control register may be used for indicating operation in a particular mode. In alternative embodiments, the video processing unit 28 operates pursuant to a mode indicated by the synchronization pulse. As shown in FIG. 4, stereoscopic or monoscopic mode may be indicated by the polarity of the synchronization pulse, the width of the synchronization pulse or other variation in characteristic of the synchronization pulse. For example, a positive synchronization pulse may indicate operation in one mode, and a negative pulse indicates operation in another mode. As another example, a wide synchronization pulse, such as 6 or more lines may indicate operation in one mode, and a normal or lesser width synchronization pulse may indicate operation in another mode. In yet other embodiments, a change in the characteristic indicates a switch in mode from a current mode to another mode.

Figure 5:
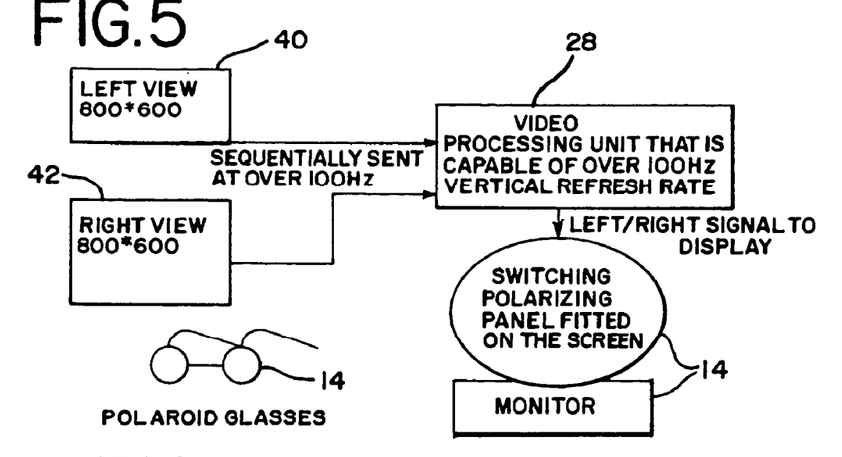
FIG. 5 is a graphical representation of another embodiment of stereoscopic viewing with an ultrasound system.

As an alternative to sub-field 44 composite frames of data 46 for the representations 40, 42, the video processing unit 28 is operable to sequentially receive the three-dimensional representations 40, 42 at an increased processing rate as represented in FIG. 5. For example, the clock rate and/or processing rate of the video processing unit 28 are increased to receive sequential frames of data at over 100 Hertz. The vertical sync rate is provided at the same rate of over 100 Hertz. For example, the different three-dimensional representations 40, 42 are sequentially provided on a same input to the video processing unit 28 each at 60 Hertz. The sequential input rate as received by the video processing unit 28 is about 120 Hertz. A vertical synchronization pulse is provided with each of the different representations 40, 42, providing an input synchronization pulse of about 120 Hertz. The representations 40, 42 may be provided without decimation or reduction in resolution. The video processing unit 28 outputs the representations 40, 42 in sequence to the display 14. In one embodiment, the video processing unit 28 includes buffers or memories operating as a page flip for sequentially loading in and outputting the representations 40, 42 at a sufficiently high rate, such as 90 Hertz or greater.

Figure 6:
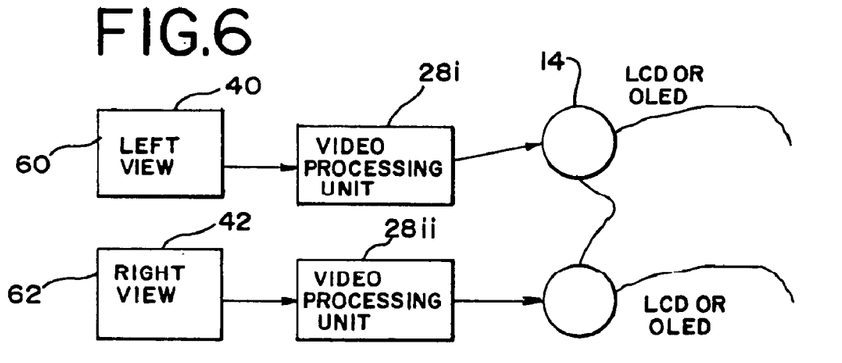
FIG. 6 is a graphical representation of yet another embodiment of stereoscopic viewing with an ultrasound system.

FIG. 6 shows yet another embodiment for operating the video processing unit 20. Separate video paths 51 and 53 are provided. Each video path includes a respective representation 40, 42 provided to a separate video processing unit 28*i*, 28*ii*. The separately processed representations 40, 42 are generated as images on the display 14. The separate video paths 51, 53 preserve temporal and spatial resolution, but may require additional hardware. For example, four buffers are provided, two buffers for inputting each of the different views 40, 42 and two buffers for outputting the different views. Further, the display 14 may be limited to a single user given a channel for each eye or viewing angle.

The video processing unit 28 is also operable to composite overlay graphics on one or more of the three-dimensional representations. For example, a first portion of an overlay graphic is composited on one three-dimensional representations at a first viewing angle, and a second portion of the overlay graphic is composited on a the other three-dimensional representation from the other viewing angle. Different portions of the overlay graphic are composited with the different three-dimensional representations. For example, in the sub-field stereo processing represented in FIG. 3, graphics are divided into even lines and odd lines. The even lines are composited with one of the decimated representations, and the odd lines are composited on the other representation. Other divisions than odd and even lines may be used. As the different views are sequentially presented to the user, the user's eye or brain integrates the graphical overlay information from the different views together to form a full resolution textual display. Visual integration may be used to recover the resolution for any displays not to be viewed in stereo.

Since different portions are composited, the graphic overlay when generated on the stereoscopic display 14 may have a monoscopic appearance. Since the three-dimensional representations are different views of a same volume, a stereoscopic display is provided with the monoscopic overlay graphic. Doppler or M-mode traces may also be divided and composited with different views as a graphical overlay for monoscopic display with stereoscopic B-mode images. In yet other alternatives, the graphical overlay is generated for stereoscopic viewing and provided with each of the different views.

The video processing unit 28 has one or more output ports. A plurality of output ports may be provided. An output port is provided for each user that may be simultaneously viewing a stereoscopic display. Alternatively, multiple users may view a same display provided on a single output port. In yet another alternative embodiment, a splitter outside of the video processing unit 28 or the ultrasound imaging system 12 allows viewing by multiple users of a same display. The output provides control signals for operating a portion of the stereoscopic display 14. For example, RGB values or other image information is provided to a monitor or display. As shown in FIG. 4, additional control signals are output by the switches 50 and 52 for operating other portions of the display 14, such as operating shutters. As another example, separate video outputs are provided for each of left and right views on stereoscopic display. In one embodiment, the output also supports two-dimensional video signals and common video formats such as NTSC/PAL and VGA/XVGA.

The user input is provided for operating the ultrasound imaging system 12. The user input is a keyboard, knobs, buttons, sliders, touch screen, mouse, trackball, touch pad or other now known or later developed device for interfacing between a user and a computer. The user input device receives input for generating different three-dimensional representations, such as an input indicating a general viewing angle. The viewing angles for the left and right eyes are then determined based on the general viewing angle. User input may also be used to indicate a selection between stereoscopic and monoscopic viewing. For example, a button or other device is provided for directly switching between two different viewing modes. As another example, the selection of software associated with three-dimensional imaging indicates switching to a stereoscopic view. As yet another example, the connection of a stereoscopic viewing device to the ultrasound imaging system 12 is provided as user input for switching to a stereoscopic viewing mode.

The stereoscopic display 14 is operable to display three-dimensional representations from two or more views substantially simultaneously. The display 14 sequentially displays different representations or displays the different representations in parallel.

The human brain can construct 3D information if motion is present for a 2D image. An automatic animation of a single image for each given time, such as sweeping through a plurality of viewing angles as a function of time, allows a user to perceive the series of three dimensional representations as a volume. The animation is of a single volume, not a real-time scanning or a cine loop playback (i.e., not 4D imaging). The 3D effect is not very good and the effect stops once the motion stops.

Stereo imaging may provide more desired 3D effect. The principle of how the human see stereo image is well understood. Each eye produces a flat 2D retinal image. The brain constructs a stereo or 3D image using both images. The slight viewing angle difference (ocular parallax) is the primary factor that the brain uses to construct the stereo image. The stereo display 14 is based on the principle of display the left representation to the left eye and the right representation to the right eye. Two approaches or general categories of stereoscopic displays are auto stereoscopic viewing and stereoscopic with a viewing apparatus.

Autostereoscopic displays 14 include holograms, volumetric display (e.g., multiple layer LCDs) and directional projection (e.g., projection of images to each eye). Other autostereoscopic displays 14 are free-viewing using a fixed focus, lenticular devices, parallax barriers (e.g., prisms), parallax illumination or a moving slit to alternately block left and right eye viewing. The autostereoscopic method may not require the use of any extra viewing apparatus, such as glasses. Autostereoscopic displays 14 may use complicated or expensive hardware to produce satisfactory results for multiple viewers. Many autostereoscopic displays 14 are generally limited to a single best viewing location and may easily cause headaches. Degradation in resolution, especially in the lateral direction, may increase rapidly if multiple viewing angles, such as viewing by different people at a same time, are desired. Another drawback of current state of the art autostereo viewing device is that they are not switchable between stereo and monoscopic display.

Other stereoscopic displays 14 include a stereoscope, head-mounted display device (e.g., LCD glasses or glasses with projectors), anaglyph (e.g., color coded glasses or viewing), polarized (e.g., spatially multiplexed or field-sequential), or sequential viewing (e.g., shutter glasses). These stereoscopic displays 14 may include a monitor, such as a CRT, LCD or projector, and an additional device, such as glasses, another monitor, or another device to interact with the monitor to provide stereoscopic viewing. The monitor is a display device spaced from the additional device, such as monitor or screen spaced from a head mounted device. The monitor displays the first and second three-dimensional representations in sequence, such as for left and right eye sequential viewing. The display is in conjunction with operation of the additional or head mounted device. Alternative stereoscopic displays now known or later developed may be used, such as motion parallax or Pulfrich effect viewing devices.

The additional device may be personal to each viewing or may operate for multiple viewers. For example, the additional device of the stereoscopic display 14 is a head mounted device, such as a helmet and visor or glasses. In one embodiment, a head mounted display or monitor is used, such as glasses with two LCD monitors on the glasses to provide the left and right eye representations to an individual viewer. In other embodiments, the head mounted device operates in conjunction with the monitor to provide a stereoscopic display of a region. For example, stereoscopic image pairs are displayed in sequence on the monitor for viewing through the additional device, such as shutter glasses or polarized glasses. A wired or wireless connection is used to control operation of the additional device in conjunction with the monitor. Out of the stereoscopic display methods that use an extra or individual viewing apparatus, field-sequential and/or polarization methods may provide high quality stereo image for viewing by multiple viewers. Each viewer has an individual additional viewing apparatus.

The polarization method uses lenses or glasses that have different polarization for the left and right eye. The monitor outputs the different representations or views with polarized light matched to the appropriate eye. For example, the monitor is a switching polarizing panel or monitor that sequentially alters between different polarizations for the different 3D representations. The light transmission rate may be decreased 50% or more due to the polarization. Polarized glasses may be cheaper and lighter than head mounted dual displays or even shutter glasses.

The field sequential method uses shutters to limit exposure to the left and right eyes in sequence with the sequential display of different 3D representations. The monitor outputs the different views in sequence at the original or input refresh rate (e.g., 60 Hz per eye or 120 Hz for all images). The additional device, such as shutter glasses, operates in sequence with the display on the monitor. For example, liquid crystal lenses alternate between opaque and transparent. An analog or digital controller is provided in the glasses to synchronize the left or right eye viewing with the display screen. The left eye is transparent and the right eye is opaque for 3D representations for the left eye, and the right eye is transparent and the left eye is opaque for 3D representations for the right eye.

A memory may be provided in the ultrasound imaging system 12 for storing the data representing the body prior to rendering and/or for storing rendered three-dimensional representations. The data is then later used to generate three-dimensional representations, such as by using a workstation at a later time. Similarly, the stored representations may be later used for display.

Figure 7:
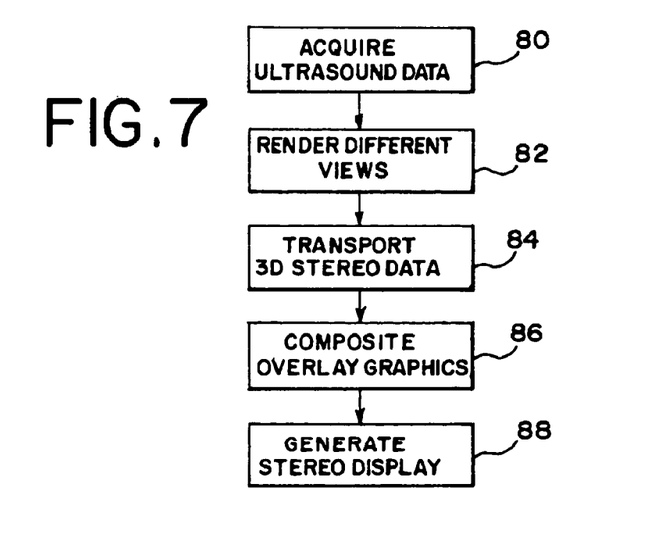
FIG. 7 is a flow chart diagram of one embodiment of a method for three dimensional viewing with an ultrasound system.

FIG. 7 shows one embodiment of a method for stereoscopic imaging during real time medical diagnostic ultrasound imaging. The method is implemented using the system of any of FIGS. 1 through 6 or other now known or later developed systems. Additional, different or fewer acts than shown on FIG. 7 may be provided, such as implementing the method without act 84 and/or act 86. The method is provided on a medical diagnostic ultrasound imaging system for use during scanning or during reviews after having performed a scan. Export of data to remote work stations may be avoided. Export of data to remote work stations for stereoscopic viewing is additionally provided in other embodiments.

In act 80, ultrasound data representing a region is acquired with an ultrasound imaging system. One or more transmit beams, plane waves or unfocussed acoustic energy is used to interrogate a volume of a body. Receive beams or information is formed in response to the transmitted acoustic energy. Data is detected from the receive beams. A volume is scanned to provide data spaced along three different dimensions. Any scan format may be provided, such as a plurality of two-dimensional scans spaced within a volume.

In act 82, the ultrasound imaging system renders different three-dimensional representations. The three-dimensional representations are of the same region or the scan region at a same or substantially same time. For example, two different viewing directions are used with the same set of detected data for rendering different three-dimensional representations for left and right eye stereo viewing. The rendering is performed once or is continuous in an ongoing process, such as rendering additional views from the same two viewing angles or different pairs of viewing angles as a function of time from more recently acquired data. More than two renderings may be provided for a same set of data, such as generating renderings from different directions or user perspectives for a same scan. If the upper-and-over method is used, the renderer may render the left and right view with half the vertical resolution to speed up the operation.

In act 84, the three-dimensional stereo data is transported. The three-dimensional stereo data is the different renderings, such as a different rendering for viewing by each eye of a user. The rendered data is provided to the display devices in one of various processes. For example, the different representations are provided on different paths through separate video processors for display. As another example, the different representations are provided sequentially on a same input or to a same video processor. The video processor is operable at the increased rate to output the stereo views at a same rate as the renderings are provided. As yet another example, different three-dimensional representations representing the same region at a substantially same time is merged into sub-fields of a same data frame. Where a resolution of each component representation is the same as a resolution operable to be handled by the display and video processing unit, each component representation is decimated by half, such as removing every other line in a vertical or horizontal direction. Other decimations or data reduction techniques may be used. Left/Right, top/bottom or other sub-field divisions may be provided for the merged data frame. The video processor receives the merged data frame. The video processor separates out the different views or three-dimensional representations from the sub-fields of the data frame for stereoscopic display. For example, the different sub-fields are separated for sequential or parallel display. A synchronization signal, such as the vertical or horizontal synchronization signal, associated with the data frame is doubled. Since the representations are received in a same data frame with a single synchronization pulse for indicating the end or beginning of each data frame, the synchronization pulse is doubled for outputting the separated representations.

In act 86, any overlay graphic is composited with the three-dimensional representations for stereoscopic views. Graphic overlay includes textual information, waveforms, M-mode displays, spectral Doppler displays, combinations thereof or other now known or later developed information. The information may be displayed monoscopically with a stereoscopic image. For example, the graphic overlay includes patient information as well as information about a current imaging configuration (e.g., frequency, transducer, type of ultrasound system, scan depth, scan format, hospital information, sonographer information, combinations thereof or other textual data).

The overlay graphic is composited with a given representation by averaging, summing, selecting a maximum intensity, overwriting or other combination techniques of video or graphic information. The combination is performed only for pixels associated with the graphic information or other information of the overlay graphic. For example, the overlay graphic information is provided on exterior regions of a two-dimensional frame while the three-dimensional representation is provided in a center region. Where the three-dimensional representation and the overlay graphic share a same pixel, such as associated with an annotation, the combination is performed to provide only the overlay graphic information for a given pixel or to provide shaded information representing both the three-dimensional representation and the overlay graphical information for a given pixel.

Since the overlay graphic may be viewed monoscopically, the content of the overlay graphic is divided between stereoscopic images. For example, odd lines of a graphic overlay are combined with a left stereoscopic image and the even lines of the overlay graphic are combined with a right stereoscopic image. When the images are viewed sequentially, a user persists the information of the overlay graphic together. In alternative embodiments, the overlay graphic is generated as a three-dimensional representation for stereoscopic viewing. The overlay graphics are then composited with each of the three-dimensional representations at a given time but from different viewing angles. The overlay graphic and the three-dimensional representation of the scan region may be simultaneously displayed in stereoscopic viewing.

Compositing the overlay graphic occurs after rendering and prior to generating images. The compositing may be performed by the video processor after receiving rendered data or may be performed by a three-dimensional processor as part of the rendering of each representation.

In act 88, a stereoscopic display is generated. The ultrasound imaging system used for acquiring the ultrasound data generates the stereoscopic display of the region. For a given time or substantially same time, two different three-dimensional representations are displayed in stereo or substantially simultaneously. For real time imaging, a sequence of pairs or stereo views are rendered and used to generate stereoscopic display. The stereo representations are provided as sequential images or images generated at a same time.

Stereoscopic views are generated using auto stereoscopic methods or methods using an additional apparatus, such as displaying the stereoscopic images on head mounted displays. As another example, sequentially generated representations or stereo views are stereoscopically displayed by viewing the representations through different polarization, switchable shutters or both polarization and shuttering. For shutter glasses, exposure of each representation to selected eyes is performed in synchronization with the generation of the corresponding images. By quickly alternating between left eye access to a left eye view and right eye access to a right eye view, a stereoscopic view or display is created. As an alternative to shutter glasses, glasses with polarization, or glasses with different color filtering mechanisms may be provided. The different views are generated with different polarization or color. By using polarizing lens in combination with the switching of a polarizing panel or other display, the different representations sequentially generated on the display are provided to different eyes of the viewer. By generating the images sequentially, such as at over 100 Hertz, a three-dimensional stereoscopic view with minimal blur, flicker, interference or undesired imaging effects is provided.

As an alternative to sequential generation of the different views, the different views or three-dimensional representations are output at a same or substantially same time. Two different displays of the two different representations are generated at the same time, such as generating the images on LCD displays or projectors on glasses limiting exposure of each of the images to a particular eye.

The same representations may be generated a plurality of times for viewing by a plurality of different users, such as generating the same representations on different LCD displays mounted on individual glasses. Alternatively, stereoscopic display is generated for a plurality of people at the same time using the same monitor or monitors. Each of the different viewers or users has associated glasses, head mounted displays or other additional apparatus for viewing the sequentially or parallel generated images stereoscopically. In yet another embodiment, multiple users view a same monitor capable of generating a three-dimensional view, such as a multilayer LCD screen.

Further acts may be provided, such as switching between monoscopic and stereoscopic modes. For example, a user selects between viewing monoscopically or stereoscopically. The same or different display device, such as a monitor or monitors, may be used for both modes of operation. During monoscopic mode, the user may remove any additional viewing apparatus to reduce interference. The switch between modes is performed in response to user input, automatically, or based on user selection of 3D or 4D imaging. The video processing unit or other hardware may receive indication of a switch as a function of the synchronization pulse. For example, the polarity of the synchronization pulse, the width of the synchronization of pulse or other characteristic is altered to indicate either a switch or a particular mode of operation.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for medical diagnostic ultrasound imaging, the system comprising:
    an ultrasound imaging system operable to generate data representing a body with an ultrasound transducer, the ultrasound imaging system comprising a three-dimensional image processor operable to render first and second three-dimensional representations as a function of the data, the first and second three-dimensional representations corresponding to first and second different viewing angles, respectively; and a stereoscopic display operable to display the first and second three-dimensional representations;

wherein the first and second three-dimensional representations are positioned in first and second sub-fields of a data frame, wherein the ultrasound imaging system further comprises:

a synchronization circuit operable to increase a vertical synchronization rate or a horizontal synchronization rate associated with the data frame; and a video processing unit operable to separate the first and second three-dimensional representations from the first and second sub-fields of the data frame and generate sequential display of the first and second three-dimensional representations as a function of the increased synchronization rate.

2. The system of claim 1 wherein the stereoscopic display comprises a head mounted device.

3. The system of claim 2 wherein the head mounted device comprises a head mounted display.

4. The system of claim 2 wherein the head mounted device comprises a shutter device, a polarized device, or combinations thereof, and wherein the stereoscopic display further comprises a display device spaced from the head mounted device, the display device operable to display the first and second three-dimensional representations in conjunction with operation of the head mounted device.

5. The system of claim 1 wherein the ultrasound imaging system comprises a transmit beamformer, a receive beamformer, a detector and a graphic overlay processor operable to generate text for at least one of the first and second three-dimensional representations.

6. The system of claim 1 wherein the video processing unit is operable to select between operation in a stereoscopic mode and a monoscopic mode as a function of a characteristic of a synchronization pulse output by the synchronization circuit.

7. The system of claim 1 wherein the stereoscopic display comprises a display and a shutter device, the display operable to display the first and second three-dimensional representations in sequence, and the shutter device operable to limit exposure to the first three-dimensional representation to a left eye and exposure to the second three-dimensional representation to a right eye.

8. The system of claim 1 wherein the video processing unit is operable to composite a first portion of an overlay graphic on the first three-dimensional representation and to composite a second portion of the overlay graphic on the second three-dimensional representation, the first portion different than the second portion.

9. The system of claim 8 wherein the first and second three-dimensional representations are of a same region, and wherein the stereoscopic display is operable to stereoscopically display the region and monoscopically display the overlay graphic with stereoscopic display of the region.

10. The system of claim 1 where the ultrasound imaging system comprises a plurality of output ports operable in conjunction with the stereoscopic display.

11. The system of claim 1 wherein the ultrasound imaging system comprises a user input, the user input controlling operation of the ultrasound imaging system and operable to select between monoscopic and stereoscopic imaging.

12. The system of claim 1 wherein the ultrasound imaging system further comprises a memory operable to (a) store the data representing the body, the three-dimensional image processor operable to render from the stored data, (b) store the first and second three-dimensional representations, the stereoscopic display operable to display as a function of the stored first and second three-dimensional representations, or (c) combinations thereof.

13. A system for medical diagnostic ultrasound imaging, the system comprising:

an ultrasound imaging system operable to generate data representing a body with an ultrasound transducer, the ultrasound imaging system comprising a three-dimensional image processor operable to render first and second three-dimensional representations as a function of the data, the first and second three-dimensional representations corresponding to first and second different viewing angles, respectively; and a stereoscopic display operable to display the first and second three-dimensional representations, wherein the ultrasound imaging system further comprises a video processing unit operable to sequentially receive the first and second three-dimensional representations at over 100 Hertz and further operable to composite a first portion of an overlay graphic on the first three-dimensional representation and to composite a second portion of the overlay graphic on the second three-dimensional representation, the first portion different from the second portion, and wherein the stereoscopic display comprises a switching polarizing panel operable to provide a different polarization for the first three-dimensional representation than for the second three-dimensional representation.

14. A method for medical diagnostic ultrasound imaging, the method comprising:

acquiring ultrasound data representing a region with an ultrasound imaging system;

rendering with the ultrasound imaging system first and second three-dimensional representations of the region from first and second, different viewing directions, respectively;

generating with the ultrasound imaging system a stereoscopic display of the region with the first and second three-dimensional representations, wherein generating comprises sequentially receiving the first and second three-dimensional representations at over 100 Hertz, and switching a polarizing panel operable to provide a different polarization for the first three-dimensional representation than for the second three-dimensional representation; and compositing a first portion of an overlay graphic on the first three-dimensional representation and compositing a second portion of the overlay graphic on the second three-dimensional representation, the first portion different than the second portion.

15. The method of claim 14 wherein generating the stereoscopic display comprises displaying on first and second head mounted displays.

16. The method of claim 14 wherein acquiring comprises generating a transmit beam, forming a receive beam in response to the transmit beam, and detecting data from the receive beam, and wherein rendering comprises rendering from the detected data.

17. The method of claim 14 further comprising:

switching between monoscopic and stereoscopic modes as a function of a characteristic of a synchronization pulse.

18. The method of claim 14 wherein the region is stereoscopically displayed and the overlay graphic is monoscopically displayed with stereoscopic display of the region.

19. The method of claim 14 wherein generating comprises generating the stereoscopic display for a plurality of people at a same time.

20. The method of claim 14 further comprising selecting between monoscopic and stereoscopic imaging in response to user input.

21. A method for medical diagnostic ultrasound imaging, the method comprising:

acquiring ultrasound data representing a region with an ultrasound imaging system;

rendering with the ultrasound imaging system first and second three-dimensional representations of the region from first and second, different viewing directions, respectively;

generating with the ultrasound imaging system a stereoscopic display of the region with the first and second three-dimensional representations;

merging the first and second three-dimensional representations into first and second sub-fields of a data frame;

doubling a vertical synchronization signal or a horizontal synchronization signal for the data frame; and separating the first and second three-dimensional representations from the first and second sub-fields of the data frame, wherein generating the stereoscopic display comprises sequentially outputting the first and second three-dimensional representations as a function of the doubled vertical or horizontal synchronization signal and limiting exposure to the first three-dimensional representation to a left eye and exposure to the second three-dimensional representation to a right eye as a function of the doubled vertical or horizontal synchronization signal.

* * * * *